United States Patent [19]
Graham et al.

[11] Patent Number: 5,510,485
[45] Date of Patent: Apr. 23, 1996

[54] 17-ESTER, AMIDE, AND KETONE DERIVATIVES OF 3-OXO-4-AZASTEROIDS AS 5A-REDUCTASE INHIBITORS

[75] Inventors: Donald W. Graham, Mountainside; Susan D. Aster, Teaneck; William Hagmann, Westfield; Richard L. Tolman, Warren, all of N.J.

[73] Assignee: Merck & Co., Inc., Rahway, N.J.

[21] Appl. No.: 335,792

[22] Filed: Nov. 10, 1994

Related U.S. Application Data

[63] Continuation-in-part of Ser. No. 886,021, May 20, 1992, abandoned.

[51] Int. Cl.$^6$ ............. C07D 241/12; A61K 31/495
[52] U.S. Cl. ............. 544/336; 544/405; 544/406; 546/77
[58] Field of Search ............. 546/77; 514/284, 514/253; 544/336

[56] References Cited

U.S. PATENT DOCUMENTS

| | | | |
|---|---|---|---|
| 4,377,584 | 3/1983 | Rasmusson | 514/284 |
| 4,732,897 | 3/1988 | Cainelli et al. | |
| 4,760,071 | 7/1988 | Rasmusson et al. | |
| 4,859,681 | 8/1989 | Rasmusson | 514/284 |
| 4,882,319 | 11/1989 | Holt | 514/119 |
| 4,888,336 | 12/1989 | Holt et al. | 546/77 |
| 5,049,562 | 9/1991 | Rasmusson et al. | 546/77 |
| 5,110,939 | 5/1992 | Holt | 548/250 |
| 5,116,983 | 5/1992 | Bhattacharya | 546/77 |
| 5,120,742 | 6/1992 | Rasmusson et al. | 514/284 |
| 5,138,063 | 8/1992 | Rasmusson et al. | |
| 5,175,155 | 12/1992 | Juniewicz et al. | 514/284 |
| 5,278,159 | 1/1994 | Bakshi et al. | |
| 5,300,294 | 4/1994 | Johnson | |
| 5,302,621 | 4/1994 | Kojima et al. | |

FOREIGN PATENT DOCUMENTS

| | | |
|---|---|---|
| 0200859 | 11/1986 | European Pat. Off. |
| 93-23051 | 11/1993 | WIPO |
| WO93/23420 | 11/1993 | WIPO |

OTHER PUBLICATIONS

Stinson, Chem. Eng. News, Jun. 29, '92 pp. 7–8.
Helliker, Wall Street Jour. 7 Jun. '91, pp. A1 and A7 (1991).
Diani et al., Jour. of Clin. & Metab. vol. 74 pp. 345–350 (1992).
Rasmusson et al. Jour Med Chem vol. 29 pp. 2298–2315 (1986).
Burger, "Medicinal Chemistry 2d Ed" Interscience N.Y., 1960 p. 42.
Rasmusson et al Jour Med Chem vol. 27 pp. 1690–1701 (1984).
Back, Jour Org Chem vol. 46 pp. 1442–1446 (1981).
Helliker, "Alopecia Sufferers Seek to Suffer Less, and Not in Silence", Wall Street Journal, 7 Jun. 1991, pp. A1 and A7.
Burger, Medicinal Chem. 2nd Ed Interscience, N.Y. 1960, p. 42.
Geldof, "Consideration of the Use of 17–Beta–N,N–diethyl Carbamoyl–4–Methyl–4–Aza–5–Alpha–Androstan–3–one (4MA) A 5–Alpha Reductase Inhibitor, in Prostate Cancer Therapy", J. Cancer Res. Clin. Oncol. 118:50–55 (1992).
Liang et al. "Species Differences in Prostatic Steroid 5alpha–reductases of Rat, Dog and Human", Endocrinology, vol. 117, No. 2, pp. 571–579 (1985).
Rasmusson et al., "Azasteroids, Structure–Activity Relationships for Inhibition of 5–alpha Reductase and of Androgen Receptor Binding", J. Med. Chem. 29: 2298–2315 (1986).
Back et al., "N–chloroazasteroids: A Novel Class of Reactive Steroid Analogous Preparation, Reaction with Thiols and Photochemical Conversion to Electrophilic N–acyl Imines", J. Org. Chem. 54: 1904–1910 (1989).
Stinson, "Prostate Drug Proscar Cleared for Marketing", Chem. Eng. News, 1992, pp. 7–8.
Diani et al., "Hair Growth Effects of Oral Administration of finasteride . . . ", Jour. Clinincal Endoc. & Metab. 74: 345–350 (1992).
Back, "Oxidation of Azasteroid Lactams and Alcohols with Benezene Selenic Anhydride", J. Org. Chem. 46: 1442–1446 (1981).
Rasmusson et al., "Azasteroids as Inhibitors of Rat Prostate 5–alpha Reductase", J. Med. Chem. 27: 1690–1701 (1984).

*Primary Examiner*—Donald G. Daus
*Attorney, Agent, or Firm*—Joanne M. Giesser; Catherine D. Fitch; Melvin Winokur

[57] ABSTRACT

Described are new 17β-ester, amide and ketone 4-aza-5a-androstan-3-ones and related compounds and their use as 5a-reductase inhibitors for treatment of benign prostatic hyperplasia and other hyperandrogenetic related disorders.

3 Claims, No Drawings

17-ESTER, AMIDE, AND KETONE DERIVATIVES OF 3-OXO-4-AZASTEROIDS AS 5A-REDUCTASE INHIBITORS

CROSS REFERENCE TO RELATED APPLICATIONS

This application is a continuation in part of application Ser. No. 886,021, filed May 20, 1992, now abandoned, and a section 371 filing of PCT/US93/04631.

BACKGROUND OF THE INVENTION

The present invention is directed to new 17β-ester, amide, and ketone derivatives of 4-aza-5a-androstan-3-ones and related compounds and the use of such compounds as 5a-reductase inhibitors.

DESCRIPTION OF THE PRIOR ART

The art reveals that certain undesirable physiological manifestations, such as ache vulgaris, seborrhea, female hirsutism, male pattern baldness and benign prostatic hyperplasia, are the result of hyperandrogenetic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri, et al., Endo., Vol. 91. No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs, e.g. the prostate, is 5a-dihydrotestosterone, and that it is formed locally in the target organ by the action of testosterone-5a-reductase. It is also known that inhibitors of testosterone-5a-reductase will serve to prevent or lessen symptoms of hyperandrogenetic stimulation.

For example, a number of 4-aza steroid compounds are known which are 5a-reductase inhibitors. See the following Merck & Co., Inc. patents, U.S. Pat. Nos. 4,377,584, 4,220,775, 4,859,681, 4,760,071 and the articles J. Med. Chem. 27, p. 1690–1701 (1984) and J. Med. Chem. 29, 2998–2315 (1986) of Rasmusson, et al., and U.S. Pat. No. 4,845,104 to Carlin. et al., and U.S. Pat. No. 4,732,897 to Cainelli, et al. which describe 4-aza-17β-substituted-5a-androstan-3-ones said to be useful in the treatment of DHT-related hyperandrogenic conditions.

Further there is the suggestion in the early prior art that hyperandrogenic diseases are the result of a single 5a-reductase. However, there are later reports regarding the presence of other 5a-reductase isozymes in both rats and humans. For example, in human prostate, Bruchovsky, et al. (See J. Clin. Endocrinol. Metab. 67, 806–816, 1988) and Hudson (see J. Steroid Biochem. 26, p 349–353, 1987) found different 5a-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5a-reductase (see J. Biol. Chem. 264 pp. 16249–55 (1989). They found a single mRNA which encodes both the liver and pro-static reductases in rats. This rat gene was later used to identify a human prostatic cDNA encoding a 5a-reductase termed "5a-reductase 1". (See Proc. Nat'l. Acad. Sci. 87, p. 3640–3644, 1990.)

More recently, a second, human prostatic reductase (5a-reductase 2) has been cloned with properties identified with the more abundant form found in crude human prostatic extracts. (See Nature, 354, p. 159–161, 1991.)

Further, "Syndromes of Androgen Resistance"—The Biology of Reproduction, Vol. 46, p. 168–173 (1992) by Jean O. Wilson suggests that the 5a-reductase 1 enzyme is associated with hair follicles.

Thus, the art supports the existence of at least two genes for 5a-reductase and two distinct isozymes of 5a-reductase in humans. Both isozymes are believed to be present in prostatic tissue in which, 5a-reductase 2, is the more abundant, while the other isozyme, 5a-reductase 1, is believed to be more abundant in scalp tissue.

In the treatment of hyperandrogenetic disease conditions, e.g. benign prostatic hyperplasia (BPH) it would be desirable to have one drug entity which is dually active against both enzymes 1 and 2 in the prostate to substantially inhibit dihydrotesterone (DHT) production. Alternatively, it would be desirable to have a drug entity which is highly selective for inhibiting the scalp-associated enzyme 5a-reductase 2. This latter drug could also be used in combination with PROSCAR® (finasteride) which is highly selective for the prostatic enzyme 5a-reductase 2 for combination therapy in the treatment of BPH.

SUMMARY OF THE INVENTION

The present invention discloses novel 17β-ester, amide, and ketone derivatives of 4-aza-5a-androstan-3-one compounds which are useful for inhibiting the 5a-reductase enzyme and isozymes thereof in prostatic tissue. They are also particularly effective in selectively inhibiting the 5a-reductase 1 associated with the scalp and/or dually inhibiting both isozymes 1 and 2 in the treatment of benign prostatic hyperplasia, acne, female hirsutism, androgenic alopecia, i.e., male pattern baldness, prostatitis, and the prevention and treatment of prostatic carcinoma.

In accordance with the present invention there is provided novel 17β-ester, amide, and ketone 4-aza-5a-androstan-3-one and related compounds of the formula (I):

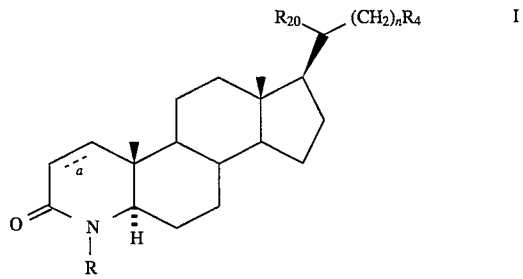

wherein:

dashed line a can represent a double bond when present;

R is selected from hydrogen, methyl, ethyl, hydroxyl, amino, and methylthio;

$R_{20}$ is selected from hydrogen or methyl;

n is an integer from 0 to 10

$R_4$ is selected from:
 (a) $COR_1$, where $R_1$ is $C_6$–$C_{10}$ aryl, substituted $C_6$–$C_{10}$ aryl, and heteroaryl;

(b) $CONHR_2$, where $R_2$ is substituted phenyl, heteroaryl, substituted heteroaryl, or $C_7$ to $C_{12}$ cycloalkyl;

(c) $CO_2R_3$, where $R_3$ is $C_6$–$C_{10}$ aryl, substituted $C_6$–$C_{10}$ aryl, or $C_7$–$C_{12}$ cycloalkyl;

where the above aryl and heteroaryl radicals can also be fused with a benzo or another heteroaryl ring and can further be substituted with one or more substituents; and pharmaceutically acceptable salts and esters thereof.

Also disclosed are processes for their preparation, pharmaceutical formulations comprising the novel compounds as active ingredients and methods of inhibiting 5a-reductases 1 and/or 2 in diseases which occur under hyperandrogenetic conditions, e.g., benign prostatic hyperplasia.

DETAILED DESCRIPTION OF THE INVENTION AND PREFERRED EMBODIMENTS

The structure I above encompasses all the 5a-reductase inhibitor compounds of this invention.

By the term $C_1$–$C_4$ alkyl is meant linear or branched alkyl; e.g. methyl, ethyl, isopropyl, propyl, n-butyl, isobutyl, sec-butyl and the like.

Dashed line "a" can independently be a double bond and when present, the compound is a delta-1-ene.

$R_1$ and $R_3$ can be a a $C_6$–$C_{10}$ aryl including phenyl, benzyl, 1- and 2-phenethyl and naphthyl.

$R_2$ can be a phenyl group.

$R_1$ and $R_2$ can also be 5–6 membered heteroaryl radicals being fully unsaturated containing 1–4 nitrogen atoms, e.g. pyridyl, pyrryl, imidazolyl, tetrazolyl, pyrazinyl, pyrimidinyl, pyrazolyl, or triazolyl; containing 1–2 oxygen or sulfur atoms, e.g. thienyl, furanyl; or in combination with 1–2 nitrogen atoms, e.g. isothiazolyl, thiazolyl, isoxazolyl, oxazolyl or thiadiazolyl; or fused with a benzo ring, e.g. quinolyl, isoquinolyl, benzothienyl, isobenzofuryl, indolyl, carbazolyl; or fused with another heteroaryl ring, e.g. purinyl, and the like.

The $C_7$–$C_{12}$ cycloalkyl in $R_2$ and $R_3$ can be 1-, 2-adamantyl, norbornyl, and bicyclo[2.2.2.]octyl.

The aryl or heteroaryl ring in $R_1$ and $R_3$ as well as the phenyl group in $R_2$ can be unsubstituted or substituted with one or more of the following substituents providing the substitution leads to a chemically inert, but biologically active 5a reductase inhibitor;

The ring substituents include:

$C_1$–$C_8$ straight or branched alkyl; e.g. methyl, ethyl, propyl, isopropyl, n-butyl, sec-butyl, isobutyl, t-butyl, n-pentyl, n-hexyl, iso-hexyl, n-butyl, n-octyl, iso-octyl, t-octyl, and the like: $C_2$–$C_8$ straight or branched alkenyl, e.g. ethenyl, 1-propenyl, 2-propenyl, 1-butenyl, 2-butenyl, 3-butenyl, 1-pentenyl, 1-hexenyl, 1-heptenyl, 1-octenyl, 2-octenyl, and the like;

$C_3$–$C_8$ cycloalkyl e.g., cyclopropyl, cyclobutyl, cyclopentyl, cyclohexyl, 1-methylcyclobutyl, cyclopentyl, cyclohexyl, 1-methylcyclohexyl, 2-methylcyclohexyl, 2-ethylcyclohexyl, and the like;

$C_2$–$C_8$ alkynyl e.g., 1-ethynyl; 1-propynyl, 2-propynyl 2-butynyl, 2-pentynyl, 1-hexynyl, 1-heptynyl, 1-octynyl;

$CONR^4R^5$ where $R^4$ and $R5$ independently are H, $C_1$–$C_8$ alkyl, as defined above, $C_3$–$C_8$ cycloalkyl as defined above, $C_1$–$C_4$ perhaloalkyl e.g., trifluoromethyl, perfluoromethyl, trichloromethyl, preferably perfluoroalkyl; phenyl; or substituted phenyl, as described below;

$COR^4$, where $R^4$ is defined above, including acetyl, isobutylcarbonyl, benzoyl and the like;

$S(O)_n$ $R^4$, where n is 0–2 and $R^4$ is defined above, including methylsulfinyl, methylsulfonyl, phenylsulfonyl, 4-chlorophenylsulfinyl and the like;

$OCOR^4$, where $R^4$ is defined above, including acetoxy, propionyloxy, benzoyloxy, 4-chlorobenzoyloxy and the like.

$SO_2NR^4R^5$ where $R^4$ and $R^5$ are described above, including sulfonamido, N-methylsulfonamido, N-phenylsulfonamido, N,N-dimethylsulfonamido and the like;

$NR^4(CO)R^5$, wherein $R^4$ and $R^5$ are defined above, including: acetylamino, benzoylamino, N-methylbenzoylamino and the like;

$NR^4(CO)NHR^5$, wherein $R^4$ and $R^5$ are described above, including; ureido, N-methylureido, N-methyl-$N^1$-phenylureido and the like;

$NHSO_2R^4$, $R^4$ being defined above, including methylsulfonylamino, phenylsulfonylamino and the like;

$OR^4$, where $R^4$ is defined above, including methoxy, phenoxy, 4-chlorophenoxy and the like, $NR^4R^5$, wherein $R^4$ and $R^5$ are described above, including amino, methylamino, dimethylamino, anilino and the like;

Cyano, nitro, halo, including: fluoro, chloro, bromo and iodo;

Perhalo $C_1$–$C_4$ alkyl, including: trifluoromethyl, perfluoroethyl, trichloromethyl and the like, $CO_2R^4$, wherein $R^4$ is defined above, including $CO_2CH_3$, $CO_2Ph$, $CO_2$-(1-adamantyl) and the like; phenyl and substituted phenyl of the formula:

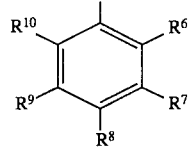

wherein the radicals $R_6$–$R_{10}$ each can represent one or more of the substituents defined above, including; hydrogen, 4-chlorophenyl, 4-fluorophenyl, 4-methoxyphenyl, 4-phenoxy and the like.

Unless otherwise indicated the 17-substituents herein described are assumed to be in the b configuration.

Representative compounds of the present invention include the following:

21-benzoyl-4-aza-5a-pregnan-3-one, 21-benzoyl-4-methyl-4-aza-5a-pregnan-3-one, 21-(2-methoxybenzoyl)-4-aza-5a-pregn-1-ene-3-one, 4-methyl-21-(2-trifluoromethylbenzoyl)-4-aza-5a-pregn-1-en- 3-one, 20-benzoyl-4-methyl-4-aza-5a-pregnan-3-one, 23-(2-fluorobenzoyl)-4-methyl-24-nor-4-aza-5a-cholane-3,23-dione, 23-(3-pyridyl)-24-nor-4-aza-5a-chol-1-ene-3,23-dione, 4-methyl-24-(2-pyridyl)-21-nor-4-aza-5a-cholane-3,24-dione, 17b-[5-(3-chlorobenzoyl)pentyl]-4-aza-5a-androstan-3-one, 17b-(6-benzoylhexyl)-4-methyl-4-aza-5a-androstan-3-one, 17b-( 10-benzoyldecyl)-4-aza-5a-androst-1-en-3-one, 4-methyl-21-(2-thienyl)-4-aza-5a-pregnane-3,21-dione, 24-(2-pyrazinyl)-4-aza-5a-chol-1-ene-3,24-dione, 4-ethyl-(2,6-dimethoxybenzoyl)-4-aza-5a-pregnan-3-one, N-(4-acetylphenyl)-4-methyl-3-oxo-4-aza-5a-pregnane-21-carboxamide, N-(4-acetylphenyl)-3-oxo-4-aza-5a-pregnane-21-carboxamide, 4-methyl-3-oxo-N-(4-pyridyl)-4-aza-5a-pregnane-21-carboxamide, 3-oxo-N-(4-pyridyl)-4-aza-5a-pregnane-21-carboxamide, N-(2-adamantyl)-3-oxo-4-aza-5a-pregnane-21-carboxamide, N-(2-adamantyl)-4-methyl-3-oxo-4-aza-5a-pregnane-21-carboxamide, 3-oxo-N-(4-pyridyl)-4-aza-5a-pregnan-21-amide, 4-methyl-3-oxo-4-(4-pyridyl)-4-aza-21-nor-5a-cholan-24-amide, 4-methyl-3-oxo-N-(3-pyridyl)-4-aza-5a-pregnane-21-carboxamide, 4-methyl-3-oxo-N-(2-pyridyl)-4-aza-5a-pregnane-21-carboxamide, N-(1-adamantyl)-4-methyl-3-oxo-4-aza-5a-pregnane-20(S)-carboxamide, N-(4-acetylphenyl)-4-methyl-3-oxo-4-aza-5a-pregnane-20(S)-carboxamide, N-(4-chlorophenyl)-4-methyl-3-oxo-4-aza-5a-cholan-24-amide, N-(4-acetylphenyl)-4-methyl-3-oxo-4-aza-5a-cholan-24-amide, 3-oxo-N-(4-trifluoromethylphenyl)-4-aza-5a-cholan-24-amide, 4-methyl-3-oxo-N-(4-pyridyl)-24-nor-4-aza-5a-cholan-24-amide, N-(1-adamantyl)-11-(4-methyl-3-oxo-4-aza-5a-androstan-17β-yl)undecanamide, N-(2-pyridyl)-6-(4-methyl-3-oxo-4-aza-5a-androstan-17β-yl)hexanamide, N-(3-pyridyl)-5-(3-oxo-4-aza-5 a-androst-1-en-17β-yl)pentanamide, N-(2-thienyl)-7-(4-methyl-3-oxo-4-aza-5a-androstan-17β-yl)heptanamide, 3-oxo-N-(2-pyrazinyl)-4-aza-5a-pregnan-21-amide, 4-methyl-3-oxo-N-(2-t-butylphenyl)-4-aza-5a-cholane-24-carboxamide, 4-methyl-3-oxo-N-(2-cyanophenyl)-4-aza-chol-1-ene-24-carboxamide, N-(2-bicyclo[2.2.2]octyl)-9-(3-oxo-4-aza-5a-androstan-17β-yl)nonanamide, 1-adamantyl 4-methyl-3-oxo-4-aza-5a-pregnane-20(S)-carboxylate, phenyl 4-methyl-3-oxo-4-oxo-4-aza-5a-pregnane-20(S)-carboxylate, 2-(t-butyl)phenyl 4-methyl-3-oxo-4-aza-5a-pregnane-21-carboxylate, 2-methoxyphenyl 4-methyl-3-oxo-4-aza-5a-pregnane-21-carboxylate, phenyl 3-oxo-4-aza-5a-pregnane-21-carboxylate, phenyl 4-methyl-3-oxo-4-aza-5a-pregnane-21-carboxylate, phenyl 5-(4-methyl-3-oxo-4-aza-5a-androstan-17β-yl)pentanoate, 2-(t-butyl)phenyl 3-oxo-4-aza-5a-pregnan-21-oate, 2,6-dimethoxyphenyl 3-oxo-4-aza-5a-pregn-1-en-21-oate, 2-adamantyl 8-(4-methyl-3-oxo-4-aza-5a-androstan-17β-yl)octanoate, 2,6-dimethylphenyl 3-oxo-4-aza-5a-pregn-1-en-21-oate, 2,6-dichlorophenyl 4-methyl-3-oxo-4-aza-5a-pregn-1-en-21-ate, phenyl 10-(4-methyl-3-oxo-4-aza-5a-androstan-17β-yl)decanoate, and also including the corresponding compounds wherein the 4-hydrogen substituent is replaced by a methyl or an ethyl radical, and/or a delta-one double bond is present.

Also included within the scope of this invention are pharmaceutically acceptable salts, i.e. hydrochloride, hydrobromide, acetate, pamoate, and the like, of the compound where a basic heteroaryl radical is present, e.g. 4-pyridyl, which can be used as the dosage form for modifying solubility or hydrolysis characteristics or for use as sustained release or prodrug formulations.

The novel compounds of formula I of the present invention are prepared by methods discussed below. The compounds and intermediates and their physical properties are listed in Table 1, and their preparation is illustrated in Examples 1–11.

The starting materials for these preparations are the appropriate carboxylic acids 1, 2, 9, 16, 17, 34, 37, 40, 45, 63, and 64. The source of these carboxylic acids is as follows:

The synthesis of acid 1 is published in J. Med. Chem. 1984, Vol. 27, p 1690.

Acid 2 was prepared by the same procedure as acid 1.

The preparation of acid 9 is published in J. Med. Chem. 1984 Vol. 27, p. 1690.

The syntheses of acids 16 and 17 are detailed in Example 1. The aldehyde 50 was reacted with the methyl (diethylphosphono)acetate anion to give the olefinic Horner-Wadsworth reaction product 51. Hydrogenation to the saturated ester 52 and saponification with aqueous KOH in methanol gave 17. The same sequence of reactions starting with the corresponding 4-methyl aldehyde (J. Med. Chem. 1986 Vol. 29, p. 2304. compound 10bg) produced the acid 16.

Acid 34 was prepared as outlined in Example 10. The nitrile 58 was transformed into the methyl ester 59 by conversion to the iminoester with anhydrous HCl in methanol followed by treatment with water. KOH saponification produced the acid 34.

The acid 37 was synthesized by the Arndt-Eistert homologation of 16. Activation of 16 as the mixed anhydride with isobutyl chloroformate and N-methyl morpholine and reaction with diazomethane gave the diazoketone 53. Silver benzoate catalyzed decomposition of 53 in methanol gave the homologous methyl ester 54. Saponification have the corresponding acid 37.

The synthesis of the acid 41 is published in J. Med. Chem. 1986 Vol. 29, p. 2300. The acids 45, 63, and 64 were prepared by the reaction sequence detailed in Example 11. Palladium catalyzed coupling of the $D^{16}$-17-triflate 60 with methyl 4-pentynoate using the procedures published in Synlett. 1991 p. 409: J. Org. Chem. 1992 Vol. 57, p. 973. gave the enyne 61. Hydrogenation catalyzed with palladium on carbon formed the saturated ester 62 and KOH saponification gave 45. Similar reaction sequences using methyl 5-hexynoate and 10-undecynoic acid gave the acids 63 and 64.

Starting with the above acids, the novel ketones, amides, and esters listed in Table 1 were prepared using the procedures discussed below and derailed in the Examples.

The synthesis of the ketones 32 and 33 are given in Examples 5 and 6. Using the procedures published in J. Med. Chem. 1986 Vol. 29, p. 2310, the acids 16 and 17 were converted into the 2-thiopyridyl esters 55 and 56 by reaction with triphenylphosphine and 2,2'-dithiodipyridine, (Example 5). Low temperature reaction of these 2-thiopyridyl esters with phenyl-magnesium chloride produced the phenyl ketones 32 and 33 (Example 6).

The amides listed in Table 1 were prepared by a variety of procedures:

For the unhindered acids 16, 17, 34, 37, 41, 62, 63, and 64, 4-dimethylaminopyridine (DMAP) catalyzed carbodiimide mediated condenstion with the appropriate amine or aniline was used. Either dicyclohexylcarbodiimide (Example 3) or the water soluble 1-(3-dimethylaminopropyl)- 3-ethylcarbodiimide hydrochloride (Example 8) could be used.

For the more hindered acids 1 and 2, formation of the mixed anhydride with isobutyl chloroformate and N-methylmorpholine followed by reaction with the appropriate amine (Example 4) proved to be the best procedure.

For the most hindered acid (9), it was necessary to activate the acid for reaction with an amine by either forming the acid chloride with oxalyl chloride (Example 9) or converting it into the 2-thiopyridyl ester (Example 5).

With hindered or unreactive amines such as 1-adamantamine or 4-acetylaniline, reaction of the 2-thiopyridyl ester alone (Example 5) or with silver trifluoromethylsulfonate catalysis (Example 7) was used to form the amide derivatives.

The ester derivatives in Table 1 were formed from the appropriate acid and alcohol or phenol using the same procedures (Examples 3, 7, and 8) used for the formation of the corresponding amide derivatives.

As outlined in Flowchart A the 4-H esters II can be converted into the corresponding $D^1$-4-H esters (III) by the procedure of Dolling, et al using dichlorodicyanobenzoquinone (J. Amer. Chem. Soc. 1988, Vol. 110, p. 3318–3319) or using benzeneselenic anhydride (J. Med. Chem. 1986 Vol. 29, p.2298–2315). Furthermore II and III can be alkylated on the 4-N with methyl or ethyl iodide using sodium hydride in DMF or DMSO to give the 4-methyl- or 4-ethyl-4H esters (IV) or the 4-methyl-or 4-ethyl-$D^1$ esters (V). Also II and III can be converted to the 4-SMe esters IV and V by reaction with sodium hydride and methanesulfenyl chloride (MeSCl). II and III can also be aminated with hydroxylamine-O-sulfonic acid and oxidized with Oxone-acetone reagent to give the 4-$NH_2$ and 4-OH esters IV and V, respectively. After saponification of the esters (II–V), the starting acids containing a 4-hydrogen, methyl, ethyl, hydroxy, amino, or methylthio substituent and either with or without a $D^1$ can be prepared. Using the procedures in Examples 1–11, these acids can be converted into the corresponding ketone, amide, and ester derivatives.

Flowchart A

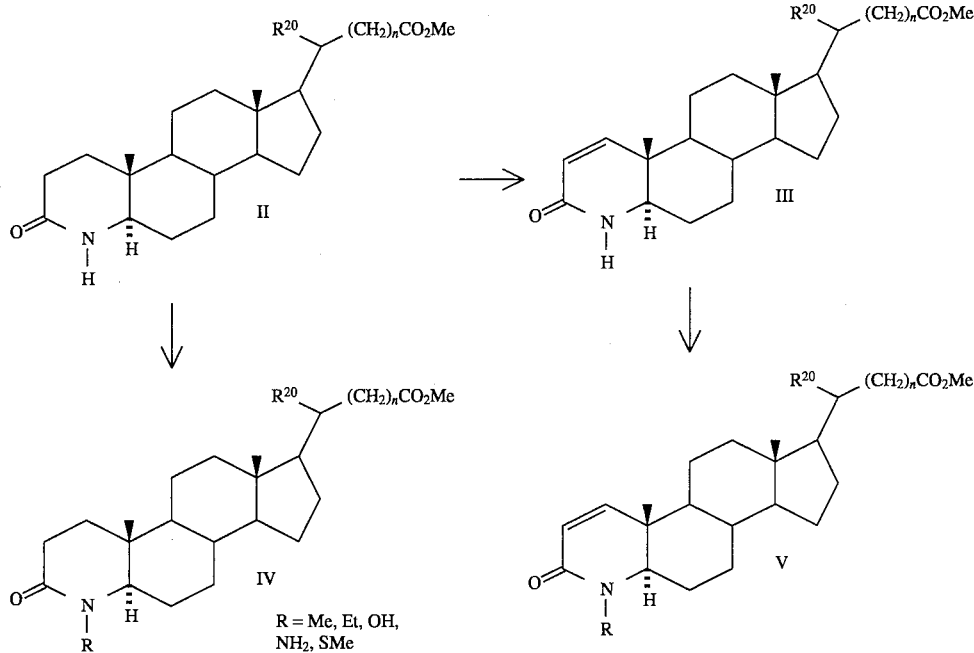

The method of preparing the novel 17-ester, amide, and ketone derivatives of 3-oxo-4-azasteroids of the present invention, already described above in general terms, may be further illustrated by the following examples.

EXAMPLE 1

3-Oxo-4-aza-5a-pregnan-21-carboxylic acid (17)

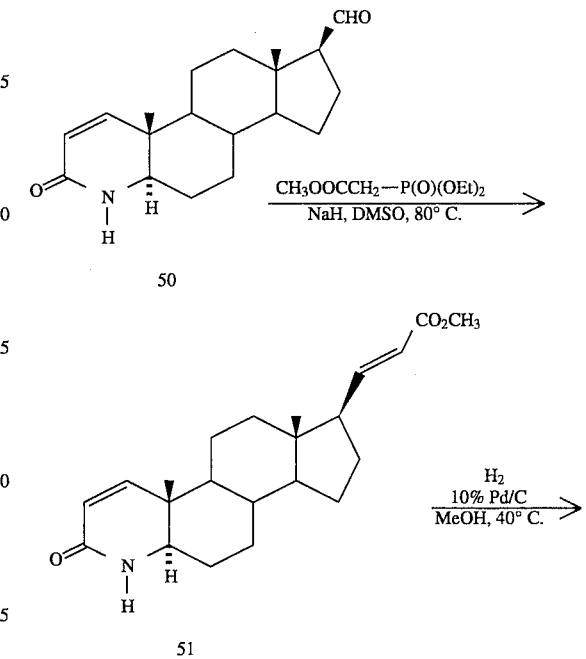

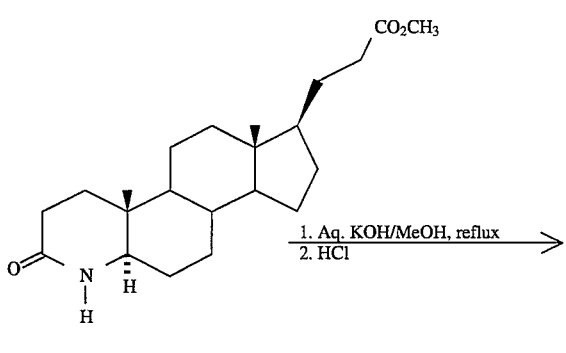

To a suspension of the aldehyde 50, (1.0 g, 3.32 mmole) in 12 ml DMSO was added 14.6 mg (3.65 mmole) sodium hydride (60% in mineral oil) and 698 ml (3.65 mmole) methyl diethylphosphonoacetate. The mixture was heated under $N_2$ atmosphere at 80° C. for 1 hr. The clear solution was cooled and partitioned between dilute HCl and methylene chloride. The organic phase wits washed with water, brine, dried over magnesium sulfate and concentrated in vacuo to give 1.2 g crude product. Purification by flash chromatography on silica gel in 4:1 methylene chloride:acetone gave 956 mg of the unsaturated ester [51, NMR, d=0.66(s, 3H, 18-Me), 0.97(s, 3H, 19-Me), 3.72(s, 3H, OMe), 5.7(d, 1H, $D^1$), 5.82(s, 1H, $D^{20}$), 5.96(bs, 1H, NH), 6.79(d, 1H, $D^1$), 6.92(dd, 1H, $D^{20}$)].

The unsaturated ester (51) (956 mg, 2.67 mmole) was dissolved in 80 ml warm methanol and hydrogenated with 300 mg 10% Pd/C at 40 psi at a temperature of 40° C. for 3 hrs. The mixture was filtered through a pad of Celite, washing with warm methanol. The flitrate was concentrated in vacuo to give 938 mg of the saturated ester (52).

The saturated ester (52) (938 mg, 2.59 mmole) was dissolved in 9 ml methanol containing 863 ml 9M KOH and refluxed for 1 hr. The mixture was concentrated to a small volume and 100 ml water added. The mixture was cooled to 10° C. and brought to pH 1 with concentrated HCl. The resulting precipitate was filtered, washed with water, sucked dry and dried in a vacuum oven at 60° C., 25 in. for 18 hrs, giving 830 mg of the acid (17).

EXAMPLE 2

3-Oxo-4-methyl-4-aza-5a-21-norcholanic acid (37)

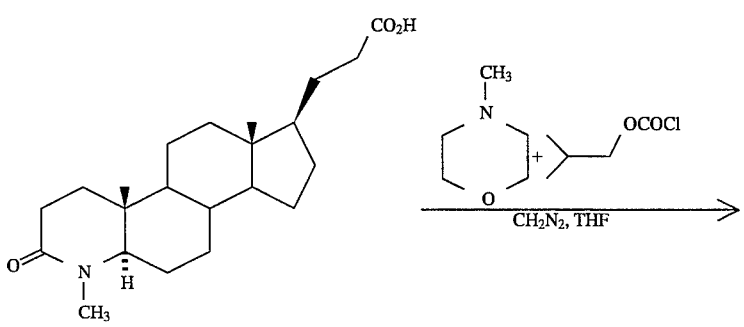

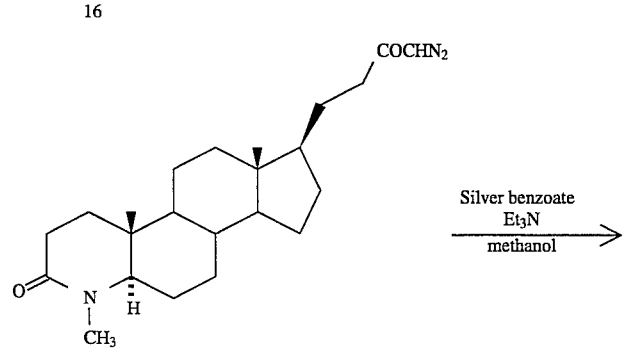

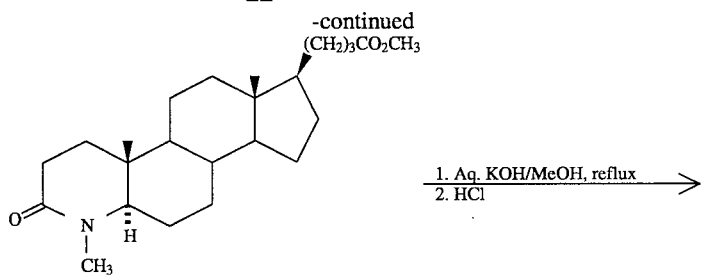

54

1. Aq. KOH/MeOH, reflux
2. HCl

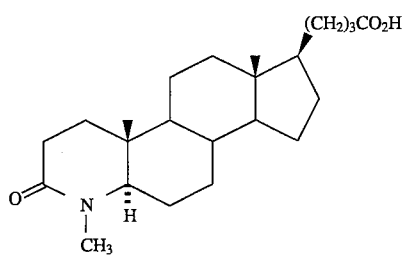

37

To a solution of the acid (16), (763 mg, 2.66 mmole) and N-methyl morpholine (296 ml, 2.66 mmole) in 60 ml THF at −20° C. under $N_2$ atmosphere was added dropwise isobutyl chloroformate (352 ml, 2.66 mmole). The mixture was stirred at −20° C. for 40 minutes, filtered and concentrated in vacuo to about ¼ its volume on a rotary evaporator using no heat. The mixture was cooled to −10° C. under $N_2$ and a freshly prepared ether solution of excess (12 mmole) diazomethane added. After stirring for 18 hours at room temperature, nitrogen was bubbled through the solution for 20 minutes (to remove excess diazomethane) and the mixture concentrated in vacuo. The residue was partitioned with methylene chloride-water and the organic phase washed with 5% acetic acid, water, brine, dried over magnesium sulfate and concentrated in vacuo to give 1.1 g crude product (oil). Purification by flash chromatography on silica gel in 4:1 methylene chloride:acetone gave 350 mg of the diazoketone (53).

The diazoketone (53), (224 mg, 0.681 mmole) was dissolved in 1 ml of methanol and 266 ml of a 0.218M solution of silver benzoate in triethyl amine (50 mg/ml) was added. The mixture was stirred at room temperature for 2 hours and the dark solution concentrated in vacuo. Methylene chloride was added and the mixture filtered. The flitrate was washed with dilute HCl, water, saturated $NaHCO_3$, brine, dried over magnesium sulfate and concentrated in vacuo to give 212 mg crude product (oil). Purification by flash chromatography on silica gel in 4:1 methylene chloride:acetone gave 153 mg of the methyl butyrate (54).

The methyl ester (54) was converted to the free acid (37) using the same conditions as was used in the previous case (52 converted to 17) except that the reflux time was 2 hours.

EXAMPLE 3

3-Oxo-4-methyl-N-phenyl-4-aza-5a-pregnan-21-carboxamide (23)

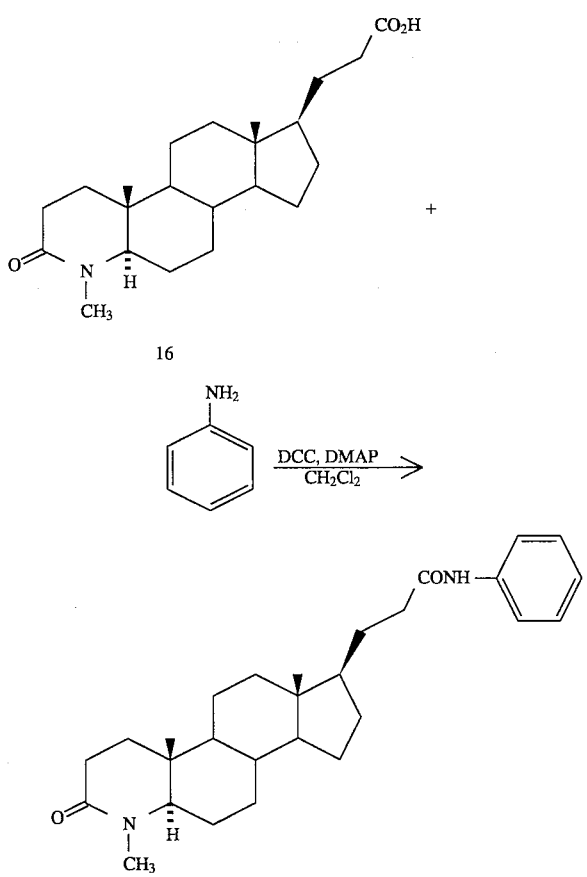

To a solution of the acid (16), (57 mg, 0.158 mmole) in 2 ml methylene chloride was added 17 ml (0.190 mmole)

aniline, 45 mg (0.220 mmole) dicyclohexylcarbodiimide (DCC) and 1 mg 4-dimethylaminopyridine (DMAP). The mixture was stirred at room temperature for 5 hours, filtered and concentrated in vacuo to give 96 mg crude mixture. Purification by preparative thin layer chromatography on a 1500 m silica gel plate in 5% methanol/methylene chloride and trituration with hexane gave 26 mg of the anilide (23).

Compounds 18–20, 24–28, 30, 38–39, 42 and 44 were prepared by the above procedure.

EXAMPLE 4

3-Oxo-4-methyl-N-phenyl-4-aza-5a-pregnan-21-amide (3)

at −20° C. for 20 minutes and aniline (64 ml, 0.70 mmoles) plus 4-dimethylaminopyridine (DMAP, 3 mg) was added. The mixture was stirred at −20° C. for 30 minutes and then at room temperature for 18 hours. The mixture was concentrated in vacuo and the residue partitioned with methylene chloride-water. The organic phase was washed with dilute HCl, water, brine, dried over magnesium sulfate and concentrated in vacuo to give 224 mg crude product. Purification by flash chromatography on silica gel in 4:1 methylene chloride:acetone gave 184 mg of the anilide (3).

Compounds 4–8, 29 and 31 were prepared by the above procedure.

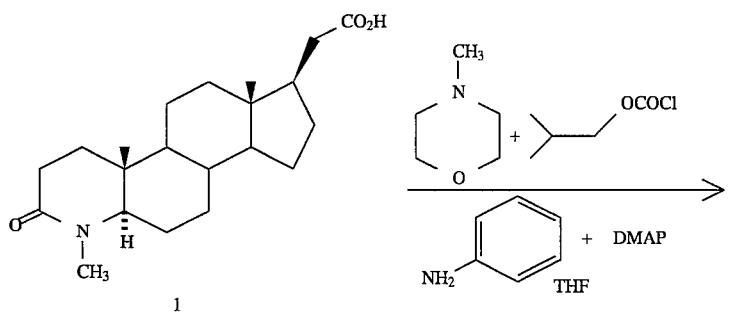

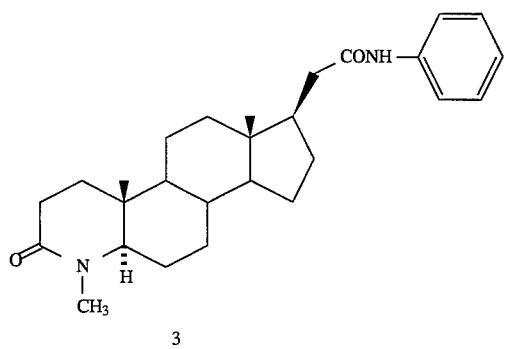

To a solution of the acid (1) (174 mg, 0.50 mmole) and N-methyl morpholine (61 ml, 0.55 mmole) in 10 ml THF at −20° C. under a $N_2$ atmosphere was added dropwise isobutyl chloroformate (66 ml, 0.50 mmole). The mixture was stirred

EXAMPLE 5

N-2-adamantyl-3-oxo-4-methyl-4-aza-5a-pregnan-21-carboxamide (21)

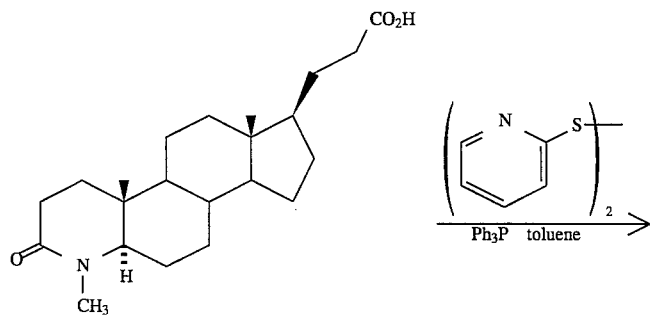

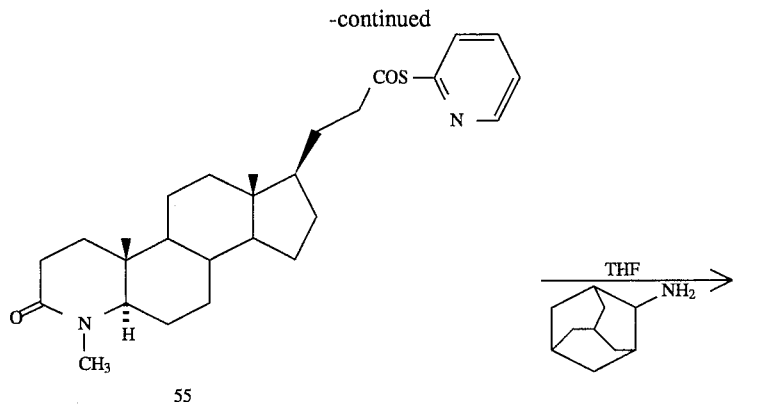

55

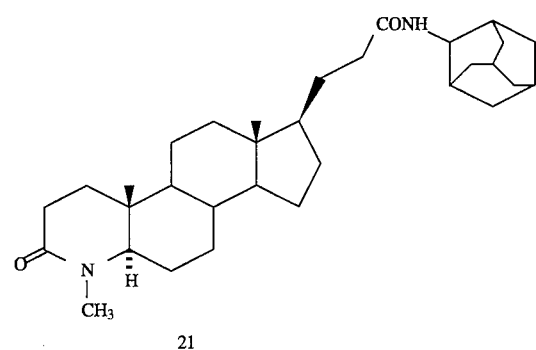

21

To a suspension of the acid (16), (391 mg, 1.08 mmole) in 3 ml toluene was added 487 mg (2.16 mmole) 2,2'-dithiodipyridine followed by 567 mg (2.16 mmole) triphenylphosphine. The mixture was stirred at room temperature for 18 hours, concentrated in vacuo and the residue flash chromatographed on silica gel in 4:1 methylene chloride-:acetone to give a yellow solid. The solid was washed with ether to give 326 mg of the thiopyridyl ester (55).

Using the same procedure, the thiopyridyl esters 56 and 57 were prepared from the carboxylic acids 17 and 9 respectively.

To a solution of the thiopyridyl ester (55), (105 mg, 0.231 mmole) in 2.5 ml THF was added 262 mg (1.73 mmole) 2-adamantane amine. The mixture was stirred at room temperature for 18 hours, concentrated in vacuo and the residue partitioned with methylene chloride-2N HCl. The organic phase was washed with water, brine, dried over magnesium sulfate and concentrated in vacuo. The residue was flash chromatographed on silica gel in 4:1 methylene chloride:acetone to give 83 mg of the amide (21).

Using the above procedure compounds 14 and 22 were prepared from the thiopyridyl esters 57 and 56 respectively.

EXAMPLE 6

21-Benzoyl-4-aza-5a-pregnan-3-one (33)

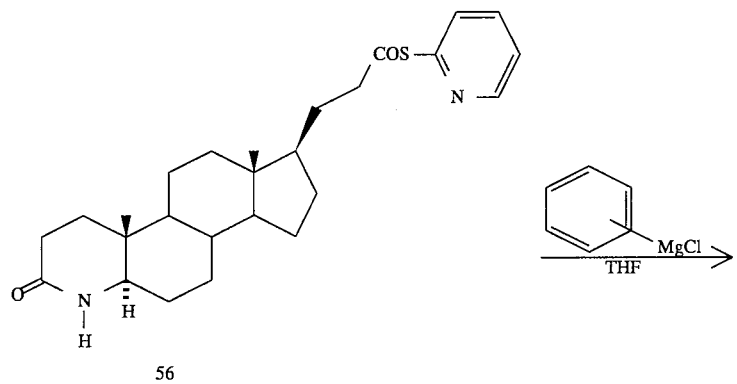

56

-continued

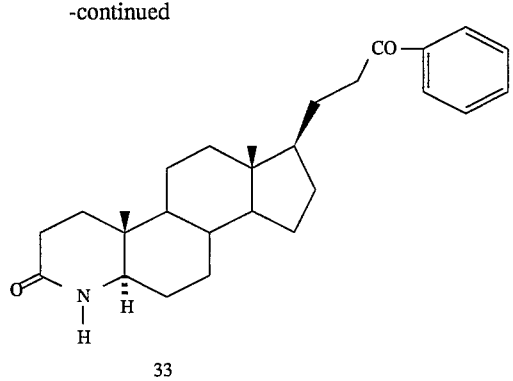

33

To a suspension of the thiopyridyl ester (56), (100 mg, 0.227 mmole) in 4 ml THF at −78° C. under a $N_2$ atmosphere was added phenyl magnesium chloride (250 ml, 0.499 mmole, 2M in THF). The mixture was stirred at −78° C. for 45 minutes and allowed to warm to 0° C. The reaction was quenched by the careful addition of 5 drops of brine. The mixture filtered and washed with THF and methylene chloride. The flitrate was concentrated in vacuo and the residue dissolved in methylene chloride, washed with 2N NaOH, water, brine, dried over magnesium sulfate and concentrated in vacuo to give 84 mg crude mixture. Purification by preparative thin layer chromatography on a 2000 m silica gel plate in 4:1 methylene chloride:acetone (run up the plate 4 times) gave 20 mg of the phenyl ketone (33).

Compound 32 was prepared by the above procedure.

EXAMPLE 7

N-(4-Acetylphenyl)-4-methyl-3-oxo-4-aza-5a-pregnane-20(S)-carboxamide (15)

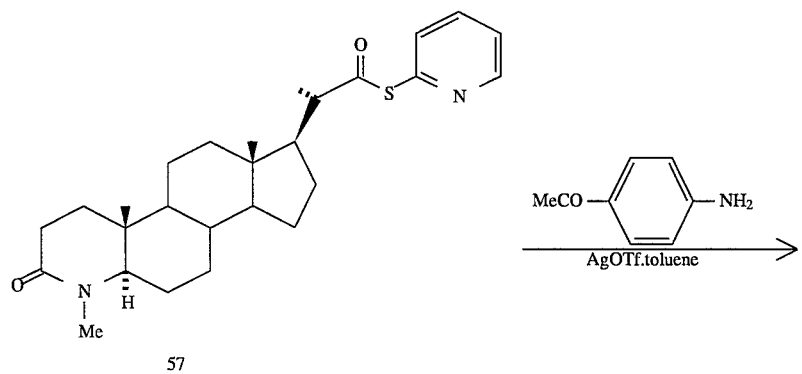

57

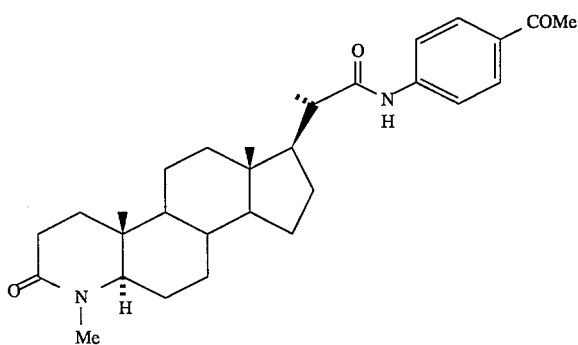

15

To a suspension of the thiopyridyl ester (57) (136 mg, 0.3 mmoles) and 4-acetylaniline (81 mg, 0.6 mmoles) in 1.5 ml of toluene was added all at once a warm solution of 93 mg (0.36 mmoles) of silver trifluoromethysulfonate in 0.6 ml of toluene. The suspension was stirred at room temperature for 24 hrs. Periodically the gummy precipitate was dispersed with a glass rod. The suspension was diluted with 30 ml of $CH_2Cl_2$ and washed with water, 5% ammonium hydroxide, water, and saturated brine and dried ($MgSO_4$). Evaporation in vacuo gave 117 mg of a pale yellow solid. Preparative TLC on two 20×20 cm, 1000 m, silica gel plates with 4:1 $CH_2Cl_2$-acetone and elution of the strongly UV-active band with 4:1 $CH_2Cl_2$-MeOH gave 32 mg of pure amide 15.

Compounds 10 and 11 were prepared by the above procedure.

EXAMPLE 8

4-Methyl-3-oxo-N-(4-pyridyl)-24-nor-4-aza-5a-cholan-23-amide (36)

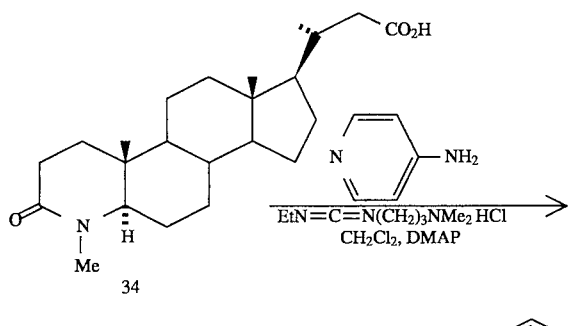

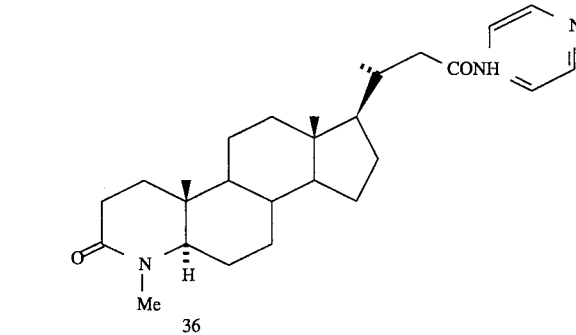

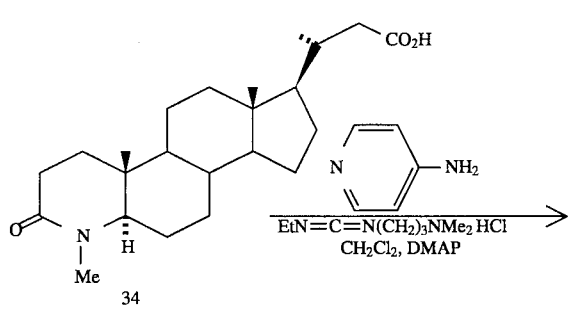

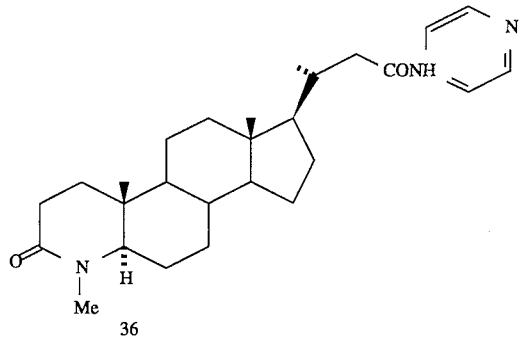

To a solution of 38 mg (0.1 mmole) of the acid 34, 19 mg (0.2 mmoles) of 4-aminopyridine, and 1 mg of 4-dimethlylaminopyridine in 0.3 ml of $CH_2Cl_2$ was added 38 mg (0.2 mmoles) of 1-(3-dimethylaminopropyl)- 3-ethylcarbodiimide hydrochloride. The solution was kept at room temperature for 24 hrs, diluted with $CH_2Cl_2$, washed with water, dilute $K_2CO_3$, water, and saturated brine and dried ($MgSO_4$). Evaporation in vacuo gave 45 mg of a gum. Preparative TLC on a 20×20 cm, 1000 m silica gel plate with 7% MeOH in $CH_2Cl_2$ and elution of the strongly UV-active band with 2:1 $CH_2Cl_2$-MeOH gave 23 mg of pure amide 36.

Compounds 35, 43, 46, 47, 48, and 49 were prepared from the appropriate acids by the above procedure.

EXAMPLE 9

N-(1-Adamantyl)-4-methyl-3-oxo-4-aza-5a-pregnane-20(S)-carboxamide (13)

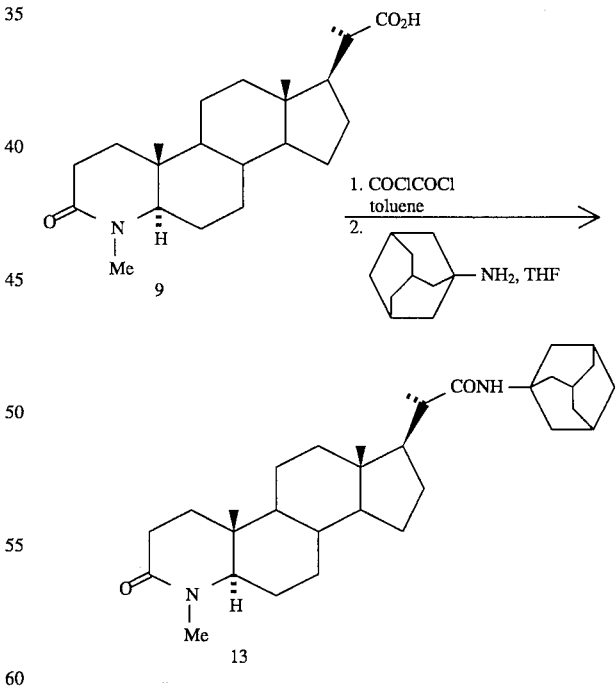

To a suspension of 108 mg (0.3 mmoles) of the acid 9 in 1.3 ml of toluene was added 0.24 ml (2.75 mmoles) of oxalyl chloride at room temperature. After 30 min the volatiles were removed in vacuo, and the residue was dissolved in 1.5 ml of THF. A solution of 181 mg (1.2 mmoles) of 1-adamantanamine and 3 mg of 4-dimethylaminopyridine in 1 ml of THF was added, and the mixture allowed to stir at room temperature for 20 hrs. Most of the THF was removed in vacuo, and the residue partitioned between ice water and $CH_2Cl_2$. The aqueous phase was extracted with $CH_2Cl_2$ (2X). The combined organic extracts were washed with 0.5N HCl, water, and dried ($MgSO_4$). Evaporation in vacuo and flash chromatography of the residue on a 10 mm×18 cm column of silica gel with 1:1 ethyl acetate-acetone gave 47 mg of pure amide 13.

EXAMPLE 10

4-Methyl-3-oxo-24-nor-4-aza-5a-cholan-23-oic acid (34)

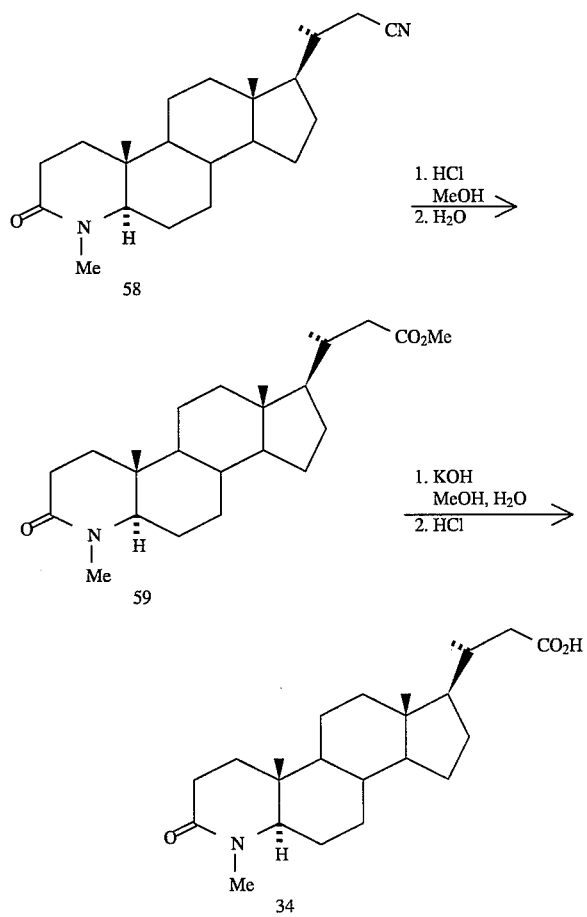

A solution of 144 mg of 4-methyl-3-oxo-24-nor-4-aza-5a-cholano-23-nitrile (58) in 5 ml of methanol saturated with anhydrous HCl was allowed to stand at room temperature for 6 hrs. The residue after evaporation in vacuo was stirred in 10 ml of water for 3 hrs and extracted with $CH_2Cl_2$ (3X). Tile extracts were washed with water and dried ($MgSO_4$). Evaporation in vacuo and flash chromatography of the residue on silica gel with 4:1 $CH_2Cl_2$-acetone gave 112 mg of methyl 4-methyl-3-oxo-24-nor-4-aza-5a-cholan-23-oate (59). The methyl ester 59 (101 mg) was saponified to 90 mg of the acid 34 using the procedure in Example 1.

EXAMPLE 11

4-Methyl-3-oxo-21-nor-4-aza-5a-cholane-24-carboxylic acid (45)

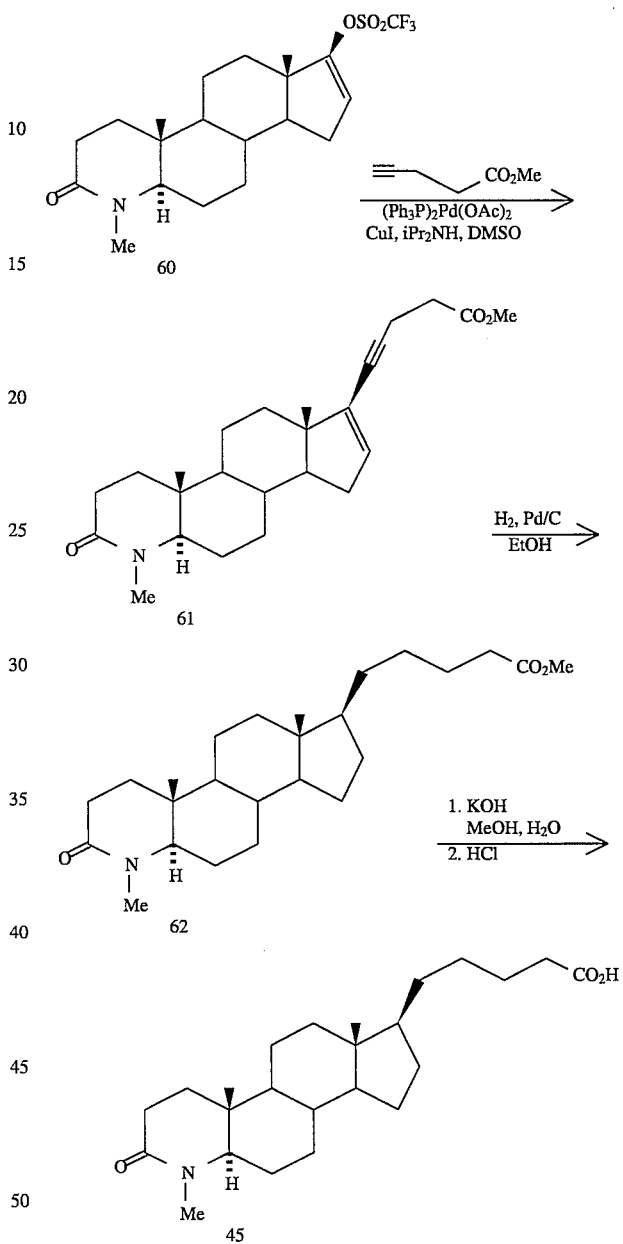

A mixture of 436 mg (1.0 mmole) of 4-methyl-17-trifluoromethylsulfonyloxy-4-aza-5a-androst-16-en-3-one (60) 168 mg (1.5 mmoles) of methyl 4-pentynoate, 40 mg of bis(triphenylphosphine)palladium(II) acetate, 5 mg of cuprous iodide in 3.0 ml of DMSO and 3.0 ml of N,N-diisopropylamine was stirred at room temperature for 17 hrs. The dark reaction mixture was poured into 50 ml of 0.5M HCl and extracted with $CH_2Cl_2$ (3X). The combined extracts were washed with water (4X) and dried ($MgSO_4$). Evaporation in vacuo and flash chromatography of the residue on silica gel with 6:1 $CH_2Cl_2$-acetone gave 400 mg of enyne 61. The enyne was immediately hydrogenated in 20 ml of EtOH with 150 mg of 10% palladium on carbon catalyst under a hydrogen-filled balloon. After stirring at room temperature for 24 hrs, the reaction mixture was filtered through a bed of Celite., which was washed with EtOH (4X). The flitrate and washes were evaportated in vacuo and the residue flash chromatographed on silica gel with 5:1 $CH_2Cl_2$ to give 345 mg of methyl 4-methyl-3-oxo-21-nor-4-aza-5a-cholane-24-carboxylate (62).

The methyl ester 62 (300 mg) was saponified to 275 mg of the acid 45 using the procedure in Example 1.

The acids 6-(4-methyl-3-oxo-4-aza-5a-androstan-17B-yl)hexanoic acid (63) and 11-(4-methyl-3-oxo-4-aza-5a-androstan-17β-yl)undecanoic acid (64) used for the preparation of the anilides 48 and 49 respectively were prepared by the above procedure.

The following table lists the compounds made in this invention and their physical properties.

The following tables 1 and 2 list some of the compounds made in this invention and their physical properties. The compound numbers in these two tables are with reference to compounds described in Examples 1 through 11.

TABLE 6

| Compd | R | $R_{20}$ | n | $R_4$ | NMR 18-Me |
|---|---|---|---|---|---|
| 1 | Me | H | 0 | $CO_2H$ | |
| 2 | H | H | 0 | $CO_2H$ | |
| 3 | Me | H | 0 | CONH—phenyl | 0.62 |
| 4 | H | H | 0 | CONH—phenyl | 0.65 |
| 5 | H | H | 0 | CONH—C6H4—COMe | 0.66 |
| 6 | H | H | 0 | CONH—C6H4—COMe | 0.66 |
| 7 | Me | H | 0 | CONH—pyridyl | 0.64 |
| 7a | Me | H | 0 | CONH(Me)—pyridyl | 0.44 |
| 8 | H | H | 0 | CONH—pyridyl | 0.62 |
| 8a | H | H | 0 | CONH(Me)—pyridyl | 0.45 |
| 9 | Me | Me | 0 | $CO_2H$ | |
| 10 | Me | Me | 0 | $CO_2$—phenyl | 0.76 |
| 11 | Me | Me | 0 | $CO_2$—adamantyl | 0.67 |
| 12 | Me | Me | 0 | CONH—CH2C(Me)3 | 0.68 |
| 13 | Me | Me | 0 | CONH—adamantyl | 0.68 |
| 14 | Me | Me | 0 | CONH—phenyl | 0.74 |
| 15 | Me | Me | 0 | CONH—C6H4—COMe | 0.72 |
| 15a | Me | Me | 0 | CONH—pyridyl | 0.71 |
| 15b | Me | Me | 0 | CONH—pyridyl | 0.72 |
| 15c | Me | Me | 0 | CONH—pyridyl | 0.71 |
| 16 | Me | H | 1 | $CO_2H$ | 0.60 |

TABLE 6-continued

| Compd | R | $R_{20}$ | n | $R_4$ | NMR 18-Me |
|---|---|---|---|---|---|
| 17 | H | H | 1 | $CO_2H$ | |
| 18 | Me | H | 1 | phenyl-$CO_2$- | 0.65 |
| 19 | Me | H | 1 | (2-MeO-phenyl)-$CO_2$- | 0.64 |
| 20 | Me | H | 1 | (t-Bu-phenyl)-$CO_2$- | 0.65 |
| 21 | Me | H | 1 | CONH-adamantyl | 0.62 |
| 22 | H | H | 1 | CONH-adamantyl | 0.62 |
| 23 | Me | H | 1 | CONH-phenyl | 0.63 |
| 24 | H | H | 1 | CONH-phenyl | 0.63 |
| 25 | Me | H | 1 | CONH-(4-COMe-phenyl) | 0.63 |
| 26 | H | H | 1 | CONH-(4-COMe-phenyl) | 0.63 |
| 27 | Me | H | 1 | CONH-(4-pyridyl) | 0.64 |
| 28 | H | H | 1 | CONH-(4-pyridyl) | 0.63 |
| 29 | Me | H | 1 | CONH-(3-pyridyl) | 0.63 |
| 30 | H | H | 1 | CONH-(3-pyridyl) | 0.62 |
| 31 | Me | H | 1 | CONH-(2-pyridyl) | 0.62 |
| 32 | Me | H | 1 | CO-phenyl | 0.64 |
| 33 | H | H | 1 | CO-phenyl | 0.63 |
| 34 | Me | Me | 1 | $CO_2H$ | 0.69 |
| 35 | Me | Me | 1 | CONH-phenyl | 0.73 |
| 36 | Me | Me | 1 | CONH-(4-pyridyl) | 0.71 |
| 37 | Me | H | 2 | $CO_2H$ | 0.58 |
| 38 | Me | H | 2 | CONH-phenyl | |
| 39 | Me | H | 2 | CONH-(3-pyridyl) | 0.59 |
| 40 | Me | Me | 2 | $CO_2H$ | |
| 41 | H | Me | 2 | $CO_2H$ | 0.65 |
| 42 | Me | Me | 2 | CONH-phenyl | 0.68 |

TABLE 6-continued

| Compd | R | $R_{20}$ | n | $R_4$ | NMR 18-Me |
|---|---|---|---|---|---|
| 43 | H | Me | 2 | CONH–C₆H₅ | 0.69 |
| 44 | Me | Me | 2 | CONH–C₆H₄–COMe | 0.68 |
| 44a | Me | Me | 2 | CONH–(4-pyridyl) | 0.66 |
| 44b | Me | Me | 2 | CONH–(3-pyridyl) | 0.66 |
| 44c | Me | Me | 2 | CONH–(2-pyridyl) | 0.67 |
| 45 | Me | H | 3 | $CO_2H$ | 0.55 |
| 46 | Me | H | 3 | $CO_2$–C₆H₅ | 0.57 |
| 47 | Me | H | 3 | CONH–C₆H₅ | 0.56 |
| 48 | Me | H | 4 | CONH–C₆H₅ | 0.55 |
| 49 | Me | H | 9 | CONH–C₆H₅ | 0.56 |
| 52 | H | H | 1 | $CO_2Me$ | 0.61 |
| 53 | Me | H | 1 | $COCHN_2$ | |
| 54 | Me | H | 2 | $CO_2Me$ | 0.58 |
| 55 | Me | H | 1 | COS–(2-pyridyl) | 0.62 |
| 56 | H | H | 1 | COS–(2-pyridyl) | 0.64 |
| 57 | Me | Me | 0 | COS–(2-pyridyl) | 0.74 |
| 58 | Me | Me | 1 | CN | |
| 59 | Me | Me | 1 | $CO_2Me$ | 0.70 |
| 59a | H | Me | 2 | $CO_2Me$ | 0.64 |
| 62 | Me | H | 3 | $CO_2Me$ | 0.56 |
| 64 | Me | H | 9 | $CO_2H$ | 0.56 |

TABLE 6

| Cmpd | NMR 19-Me | Other | Mass Spectrum |
|---|---|---|---|
| 1 | | J. Med. Chem. 1984, 27, 1690–1701. | |
| 2 | | | m/e334(M+1)FAB |
| 3 | 0.84 | 7.04–7.52(m, 5H, ArH) | m/e423(M+1)FAB |
| 4 | 0.91 | 7.07–7.53(m, 5H, ArH) | m/e409(M+1)FAB |
| 5 | 0.90 | 2.58(s, 3H, COMe); 7.61(d, 2H, ArH); 7.94(d, 2H, ArH) | m/e466(M+2)FAB |
| 6 | 0.90 | 2.57(s, 3H, COMe); 7.62(d, 2H, ArH); 7.93(d, 2H, ArH) | m/e451(M+1)FAB |
| 7 | 0.90 | 7.56(d, 2H, ArH); 8.46(d, 2H, ArH) | m/e424(M+1)FAB |
| 7a | 0.85 | 3.30(s, 3H, NMe); 7.13(d, 2H, ArH); 8.65(d, 2H, ArH) | |
| 8 | 0.88 | 7.58(d, 2H, ArH); 8.44(d, 2H, ArH) | m/e410(M+1)FAB |
| 8a | 0.87 | 3.27(s, 3H, NMe); 7.15(d, 2H, ArH); 8.66(d, 2H, ArH) | m/e423(M)EI |
| 9 | | J. Med. Chem. 1984, 27 1690–1701 | |

TABLE 6-continued

| Cmpd | NMR 19-Me | Other | Mass Spectrum |
|---|---|---|---|
| 10 | 0.91 | 1.36(s, 3H, 21-Me); 7.0–7.5(m, 5H, ArH) | |
| 11 | 0.88 | 1.13(d, 3H, 21-Me); 1.64, 2.09, 2.14(bs, 15H, adamantylH); | |
| 12 | 0.90 | 1.03(s, 9H, CMe3); 1.12(d, 3H, 21-Me); 1.40, 1.42(s, 6H, NCMe2); 5.20(s, 1H, NH) | |
| 13 | 0.89 | 1.14(d, 3H, 21-Me); 1.67, 1.99, 2.06(bs, 15H, adamantylH); 5.03(bs, 1H, NH) | |
| 14 | 0.90 | 1.28(d, 3H, 21-Me); 7.06–7.70(m, 5H, ArH) | |
| 15 | 0.89 | 1.28(d, 3H, 21-Me); 2.58(s, 3H, COMe); 7.68(d, 2H, ArH); 7.92(d, 2H, ArH); 8.00(bs, 1H, NH) | |
| 15a | 0.89 | 1.27(d, 3H, 21-Me); 7.64(d, 2H, ArH); 8.44(d, 2H, ArH); 8.50(s, 1H, NH) | |
| 15b | 0.89 | 1.29(d, 3H, 21-Me); 7.28(m, 1H, ArH); 7.92(s, 1H, ArH); 8.30(m, 2H, ArH); 8.61(bs, 1H, NH) | |
| 15c | 0.88 | 1.28(d, 3H, 21-Me); 7.04(m, 1H, ArH); 7.78(m, 1H, ArH); 8.13(m, 3H, ArH+NH) | |
| 16 | 0.90 | | m/e361(M)EI |
| 17 | | | m/e347(M)EI |
| 18 | 0.90 | 7.05–7.41(m, 5H, ArH) | m/e437(M)EI |
| 19 | 0.89 | 3.81(s, 3H, OMe); 6.90–7.29(m, 4H, ArH) | |
| 20 | 0.90 | 1.35(s, 9H, CMe3); 6.95–7.43(m, 4H, ArH) | |
| 21 | 0.90 | | m/e495(M+1)FAB |
| 22 | 0.91 | | m/e481(M+1)FAB |
| 23 | 0.89 | 7.05–7.54(m, 5H, ArH) | m/e436(M)EI |
| 24 | 0.91 | 7.06–7.55(m, 5H, ArH) | m/e422(M)EI |
| 25 | 0.89 | 2.56(s, 3H, COMe); 7.64(d, 2H, ArH); 7.93(d, 2H, ArH) | m/e478(M)EI |
| 26 | 0.91 | 2.57(s, 3H, COMe); 7.63(d, 2H, ArH); 7.91(d, 2H, ArH) | m/e464(M)EI |
| 27 | 0.90 | 7.84(d, 2H, ArH); 8.43(d, 2H, ArH) | m/e437(M)EI |
| 28 | 0.91 | 7.58(d, 2H, ArH); 8.46(d, 2H, ArH) | m/e424(M+1)FAB |
| 29 | 0.89 | 7.30(m, 1H, ArH); 8.28(m, 2H, ArH); 8.60(s, 1H, ArH) | |
| 30 | 0.90 | 7.33(m, 1H, ArH); 8.32(m, 2H, ArH); 8.62(s, 1H, ArH) | m/e424(M+1)FAB |
| 31 | 0.89 | 7.05(m, 1H, ArH); 7.31(m, 1H, ArH); 8.24(m, 2H, ArH) | |
| 32 | 0.91 | 7.38–7.62(m, 3H, ArH); 7.95(d, 2H, ArH) | |
| 33 | 0.90 | 7.05–7.54(m, 5H, ArH) | m/e408(M+1)FAB |
| 34 | 0.86 | 1.01(d, 2H, 21-Me) | |
| 35 | 0.89 | 1.04(d, 3H, 21-Me); 7.03–7.62(m, 5H, ArH); 7.21(bs, 1H, NH) | |
| 36 | 0.87 | 1.01(d, 3H, 21-Me); 7.60(bs, 2H, ArH); 8.40(s, 1H, NH); 8.44(bs, 2H, ArH) | |
| 37 | 0.90 | | m/e376(M+1)FAB |
| 38 | 0.87 | 7.07–7.49(m, 5H, ArH) | m/e451(M+1)FAB |
| 39 | 0.89 | 7.58(d, 2H, ArH); 8.46(d, 2H, ArH) | m/e451(M+1)FAB |
| 40 | | J. Med. Chem. 1986, 29 2298-2315 | |
| 41 | 0.88 | 0.91(d, 3H, 21-Me) | |
| 42 | 0.89 | 0.96(d, 3H, 21-Me); 7.03–7.56(m, 5H, ArH); 7.48(bs, 1H, NH) | |
| 43 | 0.91 | 0.96(d, 3H, 21-Me); 5.92(bs, 1H, NH); 7.04–7.64(m, 5H, ArH) | |
| 44 | 0.89 | 0.96(d, 3H, 21-Me); 2.57(s, 3H, COMe); 7.66(d, 2H, ArH); 7.90(d, 2H, ArH); 8.16(bs, 1H, NH) | |
| 44a | 0.88 | 0.94(d, 3H, 21-Me); 7.60(d, 2H, ArH); 8.37(s, 1H, NH); 8.44(d, 2H, ArH) | |
| 44b | 0.88 | 0.96(d, 3H, 21-Me); 7.33(m, 1H, ArH); 8.02(bs, 1H, ArH); 8.33(m, 2H, ArH); 8.64(s, 1H, NH) | |
| 44c | 0.87 | 0.95(d, 3H, 21-Me); 7.08(m, 1H, ArH); 7.78(m, 1H, ArH); 8.25(m, 2H, ArH); 8.68(bs, 1H, NH) | |
| 45 | 0.87 | 2.31(t, 2H, CH2CO2) | |
| 46 | 0.88 | 2.53(t, 2H, CH2CO2); 7.02–7.38(m, 5H, ArH) | |
| 47 | 0.87 | 2.33(t, 2H, CH2CO2); 7.05–7.52(m, 5H, ArH); 7.21(s, 1H, NH) | |
| 48 | 0.87 | 2.33(t, 2H, CH2CO2); 7.05– | |

TABLE 6-continued

| Cmpd | NMR 19-Me | Other | Mass Spectrum |
|---|---|---|---|
| | | 7.52(m, 5H, ArH); 7.23(s, 1H, NH) | |
| 49 | 0.88 | 2.33(t, 2H, CH2CO2); 7.05–7.54(m, 5H, ArH) | |
| 52 | 0.90 | 3.66(s, 3H, OMe); 5.83(bs, 1H, NH) | |
| 53 | | IR, 2140cm–1N2 | |
| 54 | 0.90 | 2.30(t, 2H, CH2CO2); 3.69(s, 3H, OMe) | |
| 55 | 0.90 | 7.30(m, 1H, ArH); 7.70(m, 2H, ArH); 8.62(m, 1H, ArH) | |
| 56 | 0.92 | 5.7(bs, 1H, NH); 7.31(m, 1H, ArH); 7.71(m, 2H, ArH); 8.63(m, 1H, ArH) | |
| 57 | 0.90 | 1.32(d, 3H, 21-Me); 7.32(m, 1H, ArH); 7.72(m, 2H, ArH); 8.63(m, 1H, ArH) | |
| 59 | 0.88 | 0.97(d, 3H, 21-Me); 3.65(s, 3H, OMe) | |
| 59a | 0.88 | 0.91(d, 3H, 21-Me); 3.65(s, 3H, OMe); 5.77(s, 1H, NH) | |
| 62 | 0.88 | 2.29(t, 2H, CH2CO2); 3.66(s, 3H, OMe) | |
| 64 | 0.86 | 2.33(t, 2H, CH2CO2) | |

TABLE 7

[Structure: steroid nucleus with $R_{20}$ and $(CH_2)_n R_4$ substituents at C-17, N–R at position 1, and enone system]

| Compd | R20 | n | R4 | 18-Me | NMR 19-Me | Other |
|---|---|---|---|---|---|---|
| 65 | Me | 0 | CO2H | | | |
| 66 | Me | 0 | COS–(2-pyridyl) | 0.63 | 0.95 | 1.33(d, 3H, 21-Me); 5.81(d, 1H, 1-H); 6.03(bs, 1H, NH); 6.79(d, 1H, 2-H); 7.34, 7.63, 7.79, 8.64(m, 1H ea, ArH) |
| 67 | Me | 0 | CONH–(4-pyridyl) | 0.72 | 0.94 | 1.25(d, 3H, 21-Me); 5.78(d, 1H, 1-H); 6.79(d, 1H, 2-H); 7.62(d, 2H, ArH); 8.39(d, 2H, ArH) |
| 68 | H | 1 | CO2H | 0.57 | 0.87 | 5.59(d, 1H, 1-H); 6.82(d, 1H, 2-H) |
| 69 | H | 1 | CO2Me | 0.62 | 0.98 | 3.66(s, 3H, OMe); 5.82(d, 1H, 1-H); 6.82(d, 1H, 2-H); |
| 70 | H | 1 | CONH–phenyl | 0.64 | 0.98 | 5.81(d, 1H, 1-H); 6.82(d, 1H, 2-H); 7.05–7.54(m, 5H, ArH) |
| 71 | H | 1 | CONH–C6H4–OMe (para) | 0.64 | 0.97 | 3.79(s, 3H, OMe); 5.82(d, 1H, 1-H); 6.82(d, 1H, 2-H); 6.86(d, 2H, ArH); 7.42(d, 2H, ArH) |
| 72 | H | 1 | CONH–(imidazolyl) | 0.62 | 0.97 | 5.81(d, 1H, 1-H); 6.81(d, 1H, 2-H); 6.78(s, 2H, ArH) |

TABLE 7-continued

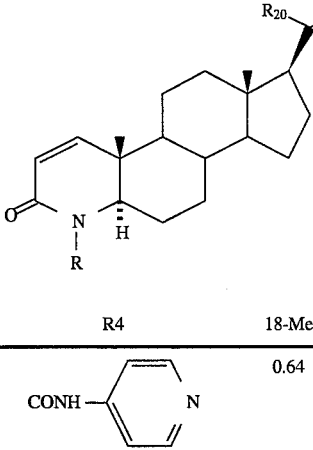

| Compd | R20 | n | R4 | NMR 18-Me | 19-Me | Other |
|---|---|---|---|---|---|---|
| 73 | H | 1 | CONH—(4-pyridyl) | 0.64 | 0.97 | 5.78(d, 1H, 1-H); 6.83(d, 1H, 2-H); 7.58(d, 2H, ArH); 8.39(d, 2H, ArH) |
| 74 | H | 1 | CONH—(3-pyridyl) | 0.63 | 0.96 | 5.78(d, 1H, 1-H); 6.79(d, 1H, 2-H); 7.28(m, 1H, ArH); 8.27(m, 2H, ArH); 8.58(s, 1H, ArH) |
| 75 | H | 1 | CONH—(2-pyridyl) | 0.64 | 0.98 | 5.81(d, 1H, 1-H); 6.81(d, 1H, 2H); 7.04(m, 1H, ArH); 7.96(m, 1H, ArH); 8.24(m, 2H, ArH) |
| 76 | H | 1 | CONH—(pyrazinyl) | 0.64 | 0.97 | 5.81(d, 1H, 1-H); 6.80(d, 1H, 2-H); 8.51(d, 1H, ArH); 8.96(d, 1H, ArH) |
| 77 | H | 1 | CONH—(3-quinolyl) | 0.64 | 0.95 | 5.82(d, 1H, 1-H); 6.86(d, 1H, 2-H); 7.52–8.06(m, 4H, ArH); 8.71–8.95(m, 2H, ArH) |
| 78 | Me | 2 | CO2H | 0.63 | 0.83 | 0.87(d, 3H, 21-Me); 5.59(d, 1H, 1-H); 6.78(d, 1H, 2-H); |
| 79 | Me | 2 | CO2Me | 0.66 | 0.95 | 0.91(s, 3H, 21-Me); 3.64(s, 3H, OMe); 5.41(s, 1H, 4-NH); 5.78(d, 1H, 1-H); 6.77(d, 1H, 2-H) |
| 80 | Me | 2 | CONH—(4-pyridyl) | 0.68 | 0.97 | 0.95(d, 3H, 21-Me); 5.46(s, 1H, 4-NH); 5.81(d, 1H, 1-H); 6.80(d, 1H, 2-H); 7.56(d, 2H, ArH); 8.13(bs, 1H, CONH); 8.46(d, 2H, ArH) |
| 81 | Me | 2 | CONH—(3-pyridyl) | 0.68 | 0.96 | 0.94(d, 3H, 21-Me); 5.58(bs, 1H, 4-NH); 5.81(d, 1H, 1-H); 6.80(d, 1H, 2-H); 7.24(m, 1H, ArH); 8.03(m, 1H, ArH); 8.22(d, 1H, ArH); 8.32(bs, 1H, ArH); 8.58(bs, 1H, CONH) |

TABLE 7-continued

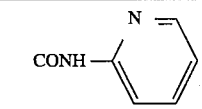

| Compd | R20 | n | R4 | NMR 18-Me | 19-Me | Other |
|---|---|---|---|---|---|---|
| 82 | Me | 2 | CONH—[pyridyl] | 0.69 | 0.96 | 0.97(d, 3H, 21-Me); 5.54(bs, 1H, 4-NH); 5.81(d, 1H, 1-H); 6.79(d, 1H, 2-H); 7.08(m, 1H, ArH); 7.76(m, 1H, ArH); 8.26(m, 2H, ArH); 8.71(bs, 1H, CONH) |
| 83 | H | 1 | COS—[pyridyl] | 0.62 | 0.97 | 5.80(d, 1H, 1-H); 6.80(d, 1H, 2-H); 7.18–7.78(m, 3H, ArH); 8.60(d, 1H, ArH) |

TABLE 7

| Compd | Mass Spectrum |
|---|---|
| 69 | m/e359(M+)EI |
| 70 | m/e420(M+)EI |
| 71 | m/e451(M+1) FAB |
| 72 | m/e410(M+)EI |
| 73 | m/e421(M+)EI |
| 74 | m/e422(M+1) FAB |
| 75 | m/e422(M+1) FAB |
| 76 | m/e423(M+)EI |
| 77 | m/e472(M+1) FAB |

The present invention has the objective of providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and treatment and prevention of prostatic carcinoma, hyperandrogenic conditions, can be administered in a wide variety of therapeutic dosage forms in conventional vehicles for systemic administration, as, for example, by oral administration in the form of tablets, capsules, solutions, or suspensions, or by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg, to 7 mg./kgs. of body weight per day. These dosages are well below the toxic dose of the product. For the treatment of androgenic alopecia, acne vulgaris, seborrhea, female hirsutism, the compounds of the present invention are administered in a pharmaceutical composition comprising the active compound in combination with a pharmacologically acceptable carrier adapted for topical, oral or parenteral administration.

These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to these of ordinary skill in the pharmaceutical arts. An effective but non-toxic amount of the compound desired can be employed as a 5 α-reductase agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

Oral dosages of the present invention, when used for the indicated effects, will range between about Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy burytic acid, polyorthoesters, polyacetals, polydihydropyrans, polycyanoacrylates and cross-linked or amphipathic block copolymers of hydrogels.

BIOLOGICAL ASSAYS

Preparation of Human prostatic and scalp 5a-reductases

Samples of human tissue were pulverized using a freezer mill and homogenized in 40 mM potassium phosphate. pH 6.5, 5 mM magnesium sulfate, 25 mM potassium chloride, 1 mM phenylmethylsulfonyl fluoride, 1 mM dithiothreitol (DTT)containing 0.25M sucrose using a Potter-Elvehjem homogenizer. A crude nuclear pellet was prepared by centrifugation of the homogenate at 1,500xg for 15 min. The crude nuclear pellet was washed two times and resuspended in two volumes of buffer. Glycerol was added to the resuspended pellet to a final concentration of 20%. The enzyme suspension was frozen in aliquots at –80° C. The prostatic and scalp reductases were stable for at least 4 months when stored under these conditions.

5α-reductase assay

The reaction mixture contained in a final volume of 100 µl is: 40 mM buffer (human scalp, potassium phosphate, pH 6.5; human prostatic 5α-reductase, sodium citrate, pH 5.5), 0.3–10 µM $^{14}$C-T (or $^{3}$H-T), 1 mM DTT, and 500 µM NADPH. Typically, the assay was initiated by the addition of 50–100 µg prostatic homogenate or 75–200 µg scalp homogenate and incubated at 37° C. After 10–50 min the reaction was quenched by extraction with 250 µl of a mixture of 70% cyclohexane: 30% ethyl acetate containing 10 mg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times DHT, 6.8–7.2 min; androstanediol, 7.6–8.0: T, 9.1–9.7 min). The HPLC system consisted of a Waters Model 680 Gradient System equipped with a Hitachi Model 655A autosampler, Applied Biosystems Model 757 variable UV detector, and a Radiomatic Model A 120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T. DHT and androstanediol.

Stumptail macaque protocol

The following protocol is utilized with the stumptail macaque monkey to demonstrate the effect of compounds of the present invention for promoting hair growth.

Twenty-one male stumptail macaque monkeys of species *Macaca speciosa* are assigned to vehicle control and drug treatment groups on the basis of baseline hair weight data. This assignment procedure is necessary to insure that the average baseline hair growth for each control and experimental group is comparable. The control and drug treatment groups are as follows:

1. Topical 50:30:20 vehicle (N=6)
2. Oral 5α-reductase and topical 50:30:20 vehicle (N=5)
3. Oral placebo (N=5)
4. 5α-reductase in vehicle (N=5)

The vehicle consists of 50% propylene glycol, 30% ethanol and 20% water. A 100 mM concentration of topical 5α-reductase is formulated in this vehicle. The same 5α-reductase is administered as an oral dose of 0.5 mg per monkey. Immediately prior to the dosing phase of the study, hair is removed from a 1 inch square area (identified by four tatoos) in the center of the balding scalp. This hair collection is the baseline hair growth determination prior to the beginning of treatment. Approximatly 250 µL of vehicle and 5α-reductase in vehicle is prepared and topically administered to the tatooed area of the scelp. The selected 5α-reductase and placebo is ingested by the monekys at the same time as the topical doses are administered. The monkeys are dosed once per day, seven days per week for twenty weeks.

At four week intervals throughout the dosing phase of the study, each monkey is shaved and the hair is collected and weighed. The body weight data (at baseline and during assay) is analyzed by the nonparametric Wilcoxon rank-sum test. Differences are significant at $p<0.05$. Hair weight data at each week collection for vehicle, placebo and treatment groups are expressed as the change from baseline. Statistical analysis is performed on the rank of the data to show overall differences among groups at each four week collection.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula:

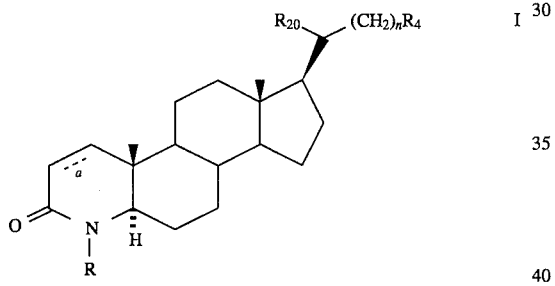

wherein:
dashed line "a" can represent a double bond when present;
R is selected from hydrogen, methyl and ethyl;
$R_{20}$ is selected from hydrogen and methyl;
n is an integer from 0 to 10;
$R_4$ is selected from:
(a) $COR_1$, where $R_1$ is $C_6-C_{10}$ aryl, substituted $C_6-C_{10}$ aryl, and heteroaryl;
(b) $CONHR_2$, where $R_2$ is substituted phenyl, heteroaryl, substituted heteroaryl, or $C_7-C_{12}$ cycloalkyl; and
(c) $CO_2R_3$, where $R_3$ is $C_6-C_{10}$ aryl, substituted $C_6-C_{10}$ aryl, or $C_7-C_{12}$ cycoalkyl;
wherein aryl is selected from phenyl, benzyl, 1-and 2-phenethyl and naphthyl;
wherein heteroaryl is selected from pyridyl, pyrryl, thienyl, isothiazolyl, thiazolyl, imidazolyl, tetrazolyl, pyrazinyl, quinolyl, isoquinolyl, benzothienyl, isobenzofuryl, pyrazolyl, indolyl, isoxazolyl, triazolyl, furanyl, oxazolyl, and thiadiazolyl;
wherein cycloalkyl is selected from 1- and 2-adamantyl, norbornyl, and bicyclo(2.2.2)octyl;
wherein the above aryl or heteroaryl radical can further be substituted with one or two substituents;
and the pharmaceutically acceptable salts thereof.

2. The compound of claim 1 wherein said aryl and heteroaryl substituents are selected from:
hydrogen;
C1–8 straight or branched alkyl;
C2–8 straight or branched alkenyl;
C3–8 cycloalkyl;
C2–8 alkynyl;
—CONR4R5 where R4 and R5 independently are H, C1–8 alkyl, C3–8 cycloalkyl, C1–4 perhaloalkyl, phenyl, or substituted phenyl, as described below;
—COR4;
—S(O)nR4 where n=0–2;
—OCOR4;
—SO2NR4R5;
—NR4(CO)R5;
—NR4(CO)NHR5;
—NHSO2R4;
—OR4;
—NR4R5;
CN;
NO2;
halo;
perhalo C1–C4alkyl;
—CO2R4;
phenyl or substituted phenyl of the formula:

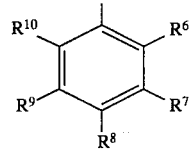

where R6–R10 independently represent one or more of the substituents as defined above.

3. The compound of claim 1 being the following:
21-benzoyl-4-aza-5a-pregnan-3-one,
21-benzoyl-4-methyl-4-aza-5a-pregnan-3-one,
21-(2-methoxybenzoyl)-4-aza-5a-pregn-1-ene-3-one,
4-methyl-21-(2-trifluoromethylbenzoyl)-4-aza-5a-pregn-1-en-3-one,
20-benzoyl-4-methyl-4-aza-5a-pregnan-3-one,
23-(2-fluorobenzoyl)-4-methyl-24-nor-4-aza-5 a-cholane- 3,23-dione,
23-(3-pyridyl)-24-nor-4-aza-5a-chol-1-ene-3,23-dione,
4-methyl-24-(2-pyridyl)-21-nor-4-aza-5a-cholane-3,24-dione,
17b-[5-(3-chlorobenzoyl)pentyl]-4-aza-5a-androstan-3-one,
17b-(6-benzoylhexyl)-4-methyl-4-aza-5a-androstan-3-one,
17b-(10-benzoyldecyl)-4-aza-5a-androst-1-en-3-one,
4-methyl-21-(2-thienyl)-4-aza-5a-pregnane-3,21-dione,
24-(2-pyrazinyl)-4-aza-5a-chol-1-ene-3,24-dione,
4-ethyl-(2,6-dimethoxybenzoyl)-4-aza-5a-pregnan-3-one,
N-(4-acetylphenyl)-4-methyl-3-oxo-4-aza-5a-pregnane-21-carboxamide,
N-(4-acetylphenyl)-3-oxo-4-aza-5a-pregnane-21-carboxamide, 4-methyl-3-oxo-N-(4-pyridyl)-4-aza-5a-pregnane-21-carboxamide, 3-oxo-N-(4-pyridyl)-4-aza-5a-pregnane-21-carboxamide, N-(2-adamantyl)-3-oxo-4-aza-5a-pregnane-21-carboxamide, N-(2-adamantyl)-4-methyl-3-oxo-4-aza-5a-pregnane-21-carboxamide, 3-oxo-N-(4-pyridyl)-4-aza-5a-pregnan-21-amide, 4-methyl-3-oxo-4-(4-pyridyl)-4-aza-21-nor-5a-cholan-24-amide, 4-methyl-3-oxo-N-(3-pyridyl)-4-aza-5a-pregnane-21-carboxamide, 4-methyl-3-oxo-N-(2-pyridyl)-4-aza-5a-pregnane-21-carboxamide, N-(1-adamantyl)-4-methyl-3-oxo-4-aza-5a-pregnane-20(S)-carboxamide, N-(4-acetylphenyl)-4-methyl-3-oxo-4-aza-5a-pregnane-20(S)-carboxamide, N-(4-chlorophenyl)-4-methyl-3-oxo-4-aza-5a-cholan-24-amide, N-(4-acetylphenyl)-4-methyl-3-oxo-4-aza-5a-cholan-24-amide, 3-oxo-N-(4-trifluoromethylphenyl)-4-aza-5 a-cholan-24-amide, 4-methyl-3-oxo-N-(4-pyridyl)-24-nor-4-aza-5a-cholan-24-amide, N-(1-adamantyl)-11-(4-methyl-3-oxo-4-aza-5a-androstan-17β-yl)undecanamide, N-(2-pyridyl)-6-(4-methyl-3-oxo-4-aza-5a-androstan-17β-yl)hexanamide, N-(3-pyridyl)-5-(3-oxo-4-aza-5a-androst-1-en-17βyl)pentanamide, N-(2-thienyl)-7-(4-methyl-3-oxo-4-aza-5a-androstan-17βyl)heptanamide, 3-oxo-N-(2-pyrazinyl)-4-aza-5a-pregnan-21-amide, 4-methyl-3-oxo-N-(2-t-butylphenyl)-4-aza-5a-cholane-24-carboxamide, 4-methyl-3-oxo-N-(2-cyanophenyl)-4-aza-chol-1-ene-24-carboxamide, N-(2-bicyclo[2.2.2]octyl)-9-(3-oxo-4-aza-5a-androstan-17β-yl)nonanamide, 1-adamantyl 4-methyl-3-oxo-4-aza-5a-pregnane-20(S)-carboxylate, phenyl 4-methyl-3-oxo-4-oxo-4-aza-5a-pregnane- 20(S)-carboxylate, 2-(t-butyl)phenyl 4-methyl-3-oxo-4-aza-5a-pregnane-21-carboxylate, 2-methoxyphenyl 4-methyl-3-oxo-4-aza-5a-pregnane-21-carboxylate, phenyl 3-oxo-4-aza-5a-pregnane-21-carboxylate, phenyl 4-methyl-3-oxo-4-aza-5a-pregnane-21-carboxylate, phenyl 5-(4-methyl-3-oxo-4-aza-5a-androstan-17β-yl)pentanoate, 2-(t-butyl)phenyl 3-oxo-4-aza-5a-pregnan-21-oate, 2,6-dimethoxyphenyl 3-oxo-4-aza-5a-pregn-1-en-21-oate, 2-adamantyl 8-(4-methyl-3-oxo-4-aza-5a-androstan-17β-yl)octanoate, 2,6-dimethylphenyl 3-oxo-4-aza-5a-pregn-1-en-21-oate, 2,6-dichlorophenyl 4-methyl-3-oxo-4-aza-5a-pregn-1-en-21-ate, phenyl 10-(4-methyl-3-oxo-4-aza-5a-androstan-17β-yl)decanoate.

\* \* \* \* \*